(12) United States Patent
Starkebaum

(10) Patent No.: US 7,580,751 B2
(45) Date of Patent: Aug. 25, 2009

(54) INTRA-LUMINAL DEVICE FOR GASTROINTESTINAL STIMULATION

(75) Inventor: Warren L. Starkebaum, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 13 days.

(21) Appl. No.: 11/118,629

(22) Filed: Apr. 29, 2005

(65) Prior Publication Data

US 2006/0247720 A1 Nov. 2, 2006

(51) Int. Cl.
*A61N 1/18* (2006.01)
(52) U.S. Cl. ........................ 607/40
(58) Field of Classification Search ............ 607/40, 607/41, 133
See application file for complete search history.

(56) References Cited

U.S. PATENT DOCUMENTS

| | | | |
|---|---|---|---|
| 6,285,897 B1 | 9/2001 | Kilcoyne et al. | |
| 6,535,764 B2* | 3/2003 | Imran et al. | 607/40 |
| 6,689,056 B1 | 2/2004 | Kilcoyne et al. | |
| 6,698,056 B1 | 3/2004 | Oretti et al. | |
| 6,754,536 B2* | 6/2004 | Swoyer et al. | 607/40 |
| 7,255,675 B2* | 8/2007 | Gertner et al. | 600/37 |
| 2002/0103424 A1 | 8/2002 | Swoyer et al. | |
| 2002/0123774 A1 | 9/2002 | Loeb et al. | |
| 2003/0018367 A1* | 1/2003 | DiLorenzo | 607/46 |
| 2003/0167024 A1 | 9/2003 | Imran et al. | |
| 2005/0209653 A1 | 9/2005 | Herbert et al. | |

OTHER PUBLICATIONS

Olympus brochure, "Single Use Rotatable Clip Fixing Devices", 4 pgs.
Wilson-Cook Medical webpage printout,GI Endoscopic, "TriClip Endoscopic Clipping Device", 1 pg.
Boston Scientific webpage printout, "Resolution Clip Device", 4 pgs.
International Search Report for PCT/US2006/015929.

* cited by examiner

*Primary Examiner*—Carl H Layno
*Assistant Examiner*—Brian T Gedeon
(74) *Attorney, Agent, or Firm*—IPLM Group, P.A.

(57) ABSTRACT

A stimulation device for electrical stimulation of a target location of a gastrointestinal tract of a patient that includes a device housing sized for introduction into a gastrointestinal tract, wherein the device housing is configured to attach to a connector, an electrical pulse generator, mounted within the device housing, to generate an electrical stimulation waveform, one or more electrodes electrically coupled to the electrical pulse generator and mounted to the device housing to deliver the electrical stimulation waveform to the gastrointestinal tract, and a fixation structure to attach the device housing to the target location of the gastrointestinal tract, wherein the stimulation device is configured to be tethered to an area around the target location using the connector. A method for attaching a stimulation device of the invention to a wall of a gastrointestinal tract is also included.

12 Claims, 10 Drawing Sheets

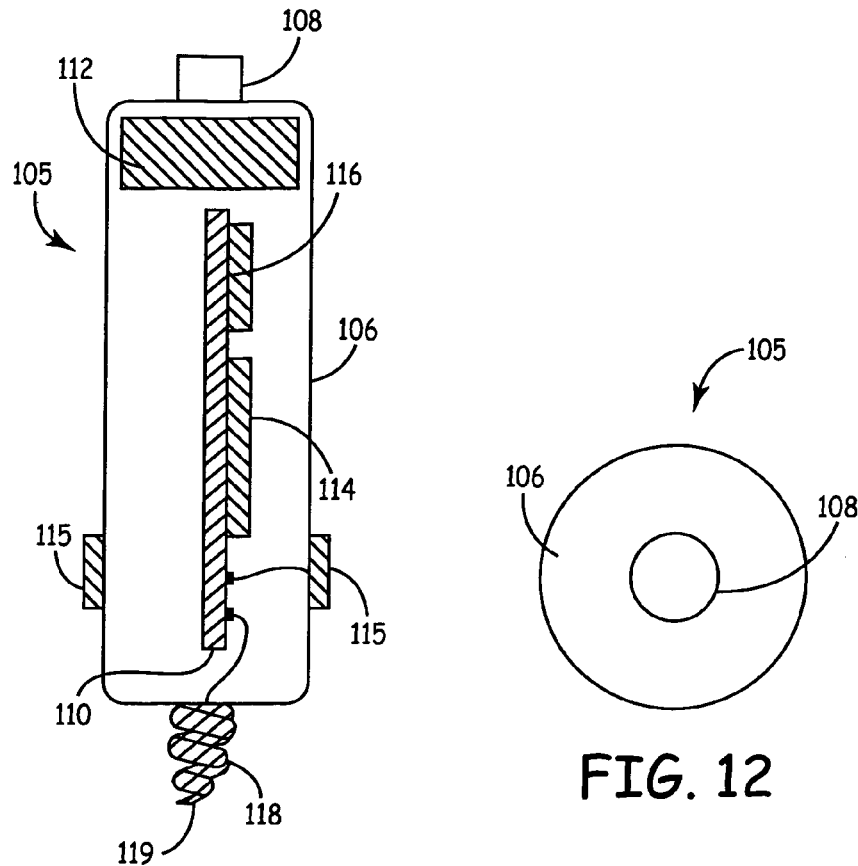
FIG. 11
FIG. 12
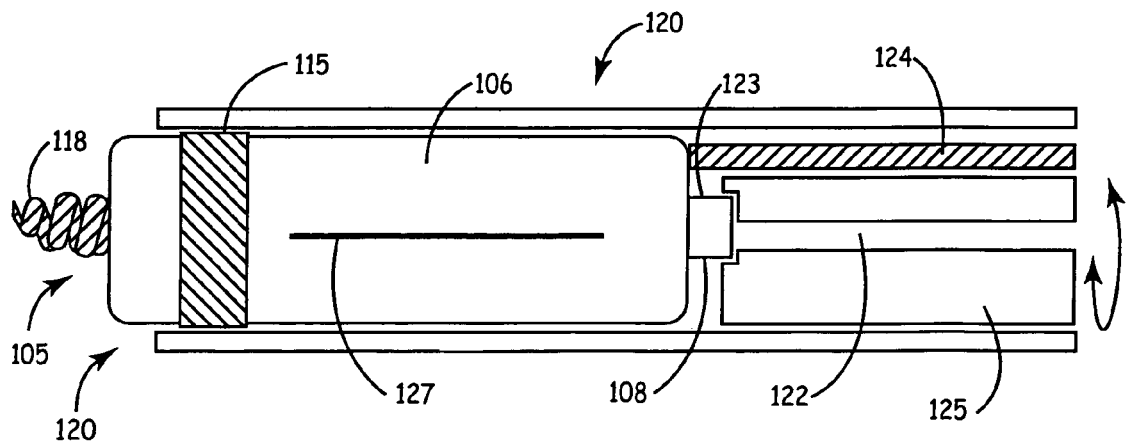
FIG. 13

INTRA-LUMINAL DEVICE FOR GASTROINTESTINAL STIMULATION

FIELD OF THE INVENTION

The invention relates to medical devices for maintaining gastrointestinal health and, more particularly, medical devices for electrical stimulation and/or electrical sensing of the gastrointestinal tract.

BACKGROUND

The gastrointestinal (GI) tract comprises the esophagus, the stomach, the small intestine, the large intestine, the colon, and the anal sphincter and is generally described as having a tract axis. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue.

Irregular contractions of any or all of the organs of the GI tract can have negative or undesirable impacts on an individual. For example, gastroparesis is an adverse medical condition in which normal gastric motor function is impaired. Gastroparesis results in delayed gastric emptying as the stomach takes too long to empty its contents. Typically, gastroparesis results when muscles within the stomach or intestines are not working normally, and movement of food through the stomach slows or stops. Patients with gastroparesis typically exhibit symptoms of nausea and vomiting, as well as gastric discomfort such as bloating or a premature or extended sensation of fullness, i.e., satiety. The symptoms of gastroparesis are the result of reduced gastric motility. Gastroparesis generally causes reduced food intake and subsequent weight loss, and can adversely affect patient health.

Electrical stimulation of the gastrointestinal tract has been used to treat symptoms of gastroparesis. For example, electrical stimulation of the gastrointestinal tract, and especially the stomach, is effective in suppressing symptoms of nausea and vomiting secondary to diabetic or idiopathic gastroparesis. Typically, electrical stimulation involves the use of electrodes implanted in the muscle wall of the target organ, e.g., the muscle wall of the stomach in the case of gastric stimulation. The electrodes are electrically coupled to an implanted or external pulse generator via implanted or percutaneous leads. The pulse generator delivers a stimulation waveform via the leads and electrodes. An example of an implanted pulse generator suitable for gastric stimulation is the ITREL 3, commercially available from Medtronic, Inc., of Minneapolis, Minn.

One method of diagnosing and/or treating various conditions of the GI tract includes electrical stimulation of some portion of the GI tract. Devices for stimulating and/or sensing the electrical activity of some portion of the GI tract can be found in the prior art.

One such device, which combines sensing and stimulating actions, can be found in commonly assigned U.S. Pat. No. 6,754,536, the disclosure of which is incorporated by reference herein. Commonly assigned U.S. patent application Ser. No. 10/801,230, filed Mar. 16, 2004 entitled "Intra-luminal devices for gastrointestinal electrical stimulation" discloses another device that can be used to stimulate and/or sense electrical activity within the GI tract. Modifying and/or enhancing their attachment mechanism(s) could improve devices such as these and others for some applications.

The present invention provides an alternative method and system for attaching devices to the inside of the GI tract

SUMMARY OF THE INVENTION

The details of one or more embodiments of the invention are set forth in the accompanying drawings and the description below. Other features, objects, and advantages of the invention will be apparent from the description and drawings, and from the claims.

One embodiment of the invention includes a stimulation device for electrical stimulation of a target location of a gastrointestinal tract of a patient, the device includes a device housing sized for introduction into a gastrointestinal tract, wherein the device housing is configured to attach to a connector, an electrical pulse generator, mounted within the device housing, to generate an electrical stimulation waveform, one or more electrodes electrically coupled to the electrical pulse generator and mounted to the device housing to deliver the electrical stimulation waveform to the gastrointestinal tract, and a fixation structure to attach the device housing to the target location of the gastrointestinal tract, wherein the stimulation device is configured to be tethered to an area around the target location using the connector.

Another embodiment of the invention includes a stimulation system for electrical stimulation of a target location of a gastrointestinal tract of a patient, the system including 1) a stimulation device that includes a device housing sized for introduction into a gastrointestinal tract of a patient, an electrical pulse generator, mounted within the device housing, to generate an electrical stimulation waveform, one or more electrodes electrically coupled to the electrical pulse generator and mounted to the device housing to deliver the electrical stimulation waveform to the gastrointestinal tract, and a fixation structure to attach the device housing to a target location within the gastrointestinal tract of the patient, 2) a connector, and 3) an attachment device, wherein the connector and the attachment device are configured to tether the stimulation device to an area near the target location.

The invention also includes a method of attaching a stimulation device to a wall of a gastrointestinal tract that includes the steps of positioning the stimulation device at a target location within the gastrointestinal tract with an endoscopic delivery device, securing the stimulation device to the target location using a fixation structure carried by the stimulation device, tethering the stimulation device to an area around the target location using at least one connector and attachment device, and withdrawing the endoscopic delivery device from the patient.

BRIEF DESCRIPTION OF THE DRAWINGS

FIG. 11 is cross-sectional side view of another stimulation device with a capsule-like structure and a screw-like fixation structure.

FIG. 12 is a top view of the device of FIG. 1.

FIG. 13 is a cross-sectional side view of the device of FIG. 11 with an endoscopic positioning probe.

DESCRIPTION OF THE PREFERRED EMBODIMENTS

Figure 1:
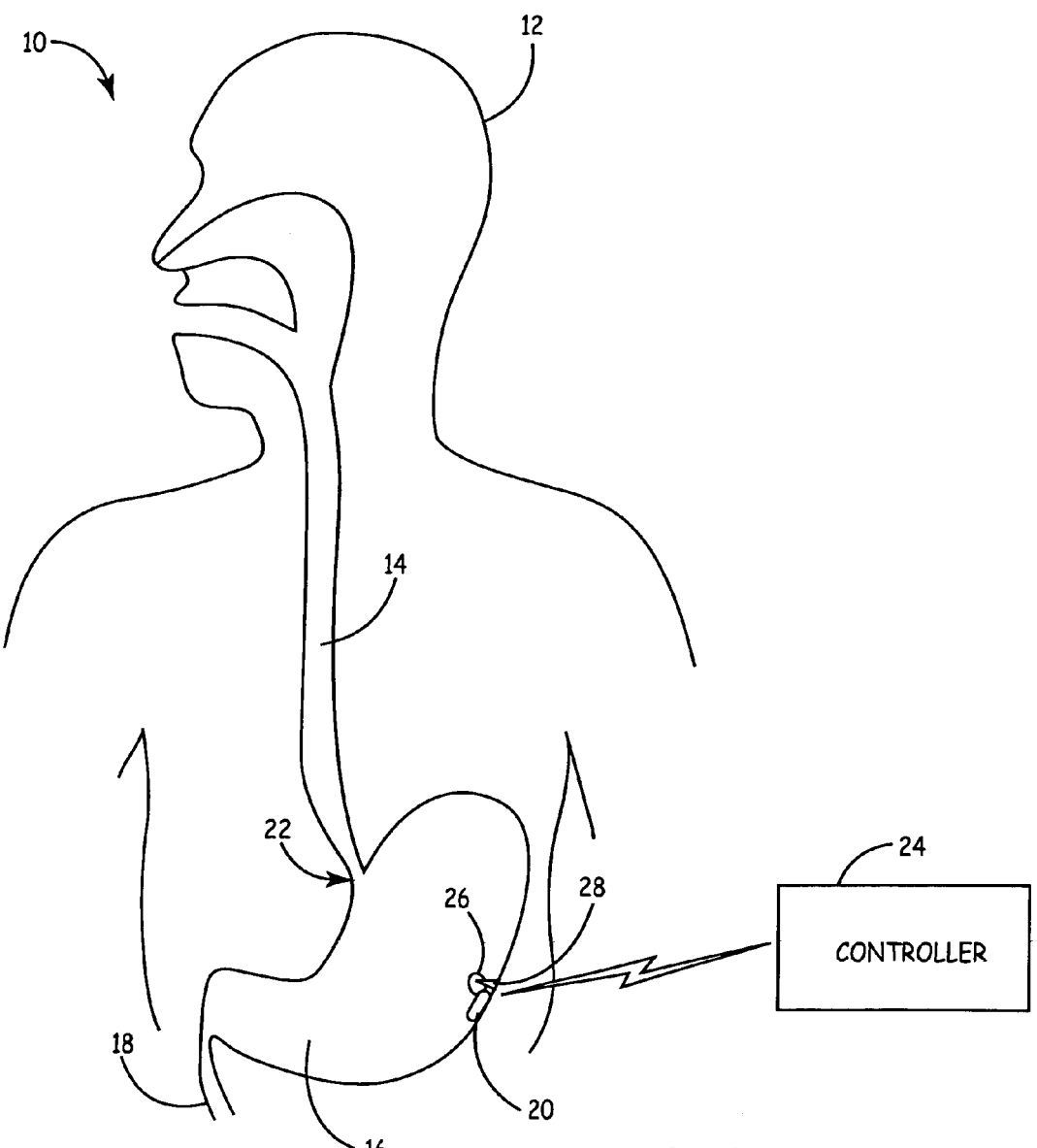
FIG. 1 is a schematic diagram illustrating a gastrointestinal electrical stimulation system shown in conjunction with a patient.

FIG. 1 is a schematic diagram illustrating a gastrointestinal electrical stimulation system 10 shown in conjunction with a patient 12. In the illustrated embodiment, stimulation system 10 delivers electrical stimulation to a target location within the gastrointestinal tract, such as the esophagus 14, stomach 16, small intestine 18, or colon (not shown). Stimulation system 10 includes a stimulation device 20, which may be placed at a target location by endoscopic delivery. In embodiments of the invention, the stimulation device 20 includes at least one connector 26 that can be tethered to the target location with at least one attachment device 28. In particular, stimulation device 20 may be delivered via the oral or nasal passage of patient 12 using an endoscopic delivery device. In the example of FIG. 1, stimulation device 20 resides within stomach 16. In this case, the endoscopic delivery device traverses esophagus 14 and then enters into stomach 16 via lower esophageal sphincter 22 of patient 12.

Figure 2:
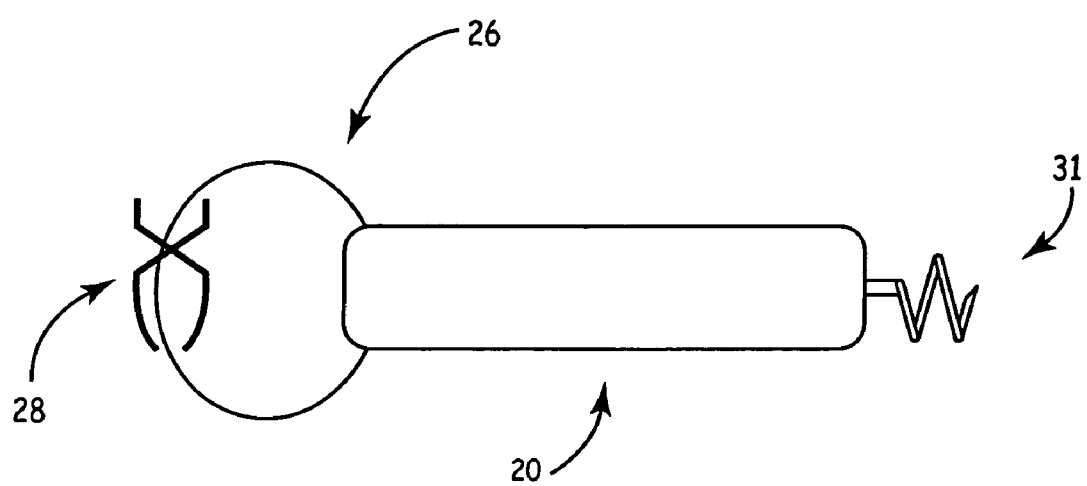
FIG. 2 is an example of a stimulation device in accordance with one embodiment of the invention.

Stimulation device 20 may have a capsule-like device housing sized for endoscopic introduction via esophagus 14 and, in some embodiments, passage through the gastrointestinal tract. For example, the capsule-like device housing of stimulation device 20 have a maximum length of less than approximately 10 mm and a maximum width of less than approximately 5 mm. In some embodiments, the device housing may be substantially cylindrical, in which case the housing may have a maximum height of less than approximately 10 mm and a maximum diameter of less than approximately 5 mm. The capsule-like device housing of stimulation device 20 includes a power source, a pulse generator, one or more electrodes, and a fixation structure 31 (shown in FIG. 2). The pulse generator produces an electrical stimulation waveform with parameters selected to suppress symptoms such as nausea and vomiting. The fixation structure 31 secures stimulation device 20 to a target location within the gastrointestinal tract. In particular, the fixation structure 31 may perforate the mucosa and lodge in the muscularis externa of the gastrointestinal tract wall when introduced against the mucosa, or grip a fold of the mucosa. The electrodes are thereby placed in contact with tissue at the target location to deliver the electrical stimulation waveform to patient 12. The capsule-like device housing may be substantially cylindrical, with a length greater than its diameter and flat or rounded ends, although the invention is not limited to any particular shape.

To place stimulation device 20, a distal end of the endoscopic delivery device can be inserted into esophagus 14 and guided to a target location within the gastrointestinal tract. The stimulation device 20. After stimulation device 20 is affixed to the target location it is tethered to the target location by affixing at least one attachment device 28 to at least one connector 26 on the simulation device. Then, the endoscopic delivery device is withdrawn from patient 12 once the stimulation device is attached to a target site. Hence, surgery is not required to place stimulation device 20 within patient 12. Moreover, following placement of stimulation device 20, there are no leads or other connections that extend outside of patient 12. On the contrary, stimulation device 20 is entirely self-contained, self-powered and integrated within a common, capsule-like housing.

Stimulation device 20 may be used to treat disorders such as nausea or vomiting or dysmotility disorders that ordinarily would require surgical implantation of an electrical stimulation system or one or more leads that extend outside the patient's body. The endoscopically placed stimulation device 20 can be used to treat short-term disorders of a few days to a few weeks, or even mid-term disorders from a few weeks to a year or more, without the need for surgery or external wires. In light of the convenience of stimulation device 20, it may even be used as a preventative treatment for nausea or vomiting associated with gastrointestinal surgery, general surgery, chemotherapy, functional dyspepsia, pregnancy, or other similar procedures known to have secondary responses such as nausea or vomiting.

The fixation structure may take any of a variety of forms, such as one or more pins, hooks, barbs, screws, sutures, clips, pincers, staples, tacks, or other fasteners. In some embodiments, the fixation structure can at least partially penetrate the mucosal lining of the gastrointestinal tract. Examples of suitable biocompatible materials for fabrication of the fixation structure include stainless steel, titanium or titanium alloys, nickel or cobalt alloys, polyethylene, nylon, PTFE, nitinol (titanium-nickel alloy), or the like.

Other examples include surgical adhesives that supplement the attachment made by the fixation structure or serve as the fixation structure itself. In other words, a pin, hook or other fixation structure may be accompanied by a biocompatible, surgical adhesive, or the adhesive may be used as the sole fixation structure without mechanical fasteners. Hence, the adhesive may work alone or in combination with a mechanical fastener.

Examples of suitable surgical adhesives for bonding the stimulation device to the mucosal lining include any of a variety of cyanoacrylates, derivatives of cyanoacrylates, or any other adhesive compound with acceptable toxicity to human gastrointestinal cells that provides the necessary adhesion properties required to secure the stimulation device 20 to the target location for a period of time sufficient for delivery of electrical stimulation. Adhesives may be injected or otherwise applied into the region surrounding the target location, e.g., via a channel within the endoscopic delivery device, or carried by the stimulation device 20 itself.

Stimulation device 20 may be configured to eventually self-detach from the target location. For example, stimulation device 20 may detach from the mucosal lining of esophagus 14 or stomach 16, when a portion of the lining held by the fixation structure sloughs away. In this case, the stimulation device 20 is free to pass through the gastrointestinal tract for excretion by the patient 12. Typically, it may be desirable that the fixation structure is effective for a period of at least a few days, and possibly up to several weeks, so that there is adequate time for delivery of electrical stimulation to treat the patient's symptoms. Alternatively, in some embodiments, stimulation device 20 may be detached by applying pressure from an endoscopic tool, or by introducing an endoscopic tool to actively cut the attachment structure and permit the stimulation device to pass through the gastrointestinal tract. In other embodiments, an endoscopic tool may be used to detach stimulation device 20 and retrieve it, i.e., remove it through the oral or nasal passage of patient 12.

In some embodiments, the fixation structure, including pins, expandable frames, and the other structures described above, may be made form a degradable material that degrades or absorbs over time at the attachment site to release stimulation device 20 from tissue at the target location. In either case, upon detachment, stimulation device 20 passes through the gastrointestinal tract of patient 12. U.S. Pat. Nos. 6,285,897 and 6,698,056 to Kilcoyne et al., the disclosure of which are incorporated herein by reference, provide examples of fixation structures for attaching monitoring devices to the lining of the esophagus, including suitable degradable materials. The fixation structures described in U.S. Pat. Nos. 6,285,897 and 6,698,056 may be suitable for attachment of stimulation device 20. The contents of U.S. Pat. Nos. 6,285,897 and 6,698,056 are incorporated herein by reference in their entireties.

Examples of suitable degradable materials for fabrication of the fixation structure or structures include bioabsorbable or dissolvable materials such as polylactic acid (PLA) or copolymers of PLA and glycolic acid, or polymers of p-dioxanone and 1,4-dioxepan-2-one, as described in U.S. Pat. Nos. 6,285,897 and 6,698,056. A variety of absorbable polyesters of hydroxycarboxylic acids may be used, such as polylactide, polyglycolide, and copolymers of lactide and glycolide, as also described in U.S. Pat. Nos. 6,285,897 and 6,698,056.

As discussed above, and depicted in FIG. 2, the stimulation device 20 also includes at least one connector 26. The at least one connector 26 provides a mechanical connection for the stimulation device 20 to the attachment device 28 when implanted. In one embodiment, the connector 26 is connected to the stimulation device 20 via a mechanical connection. For example, the stimulation device 20 could be fabricated with a structure that affords connection to the connector 26. In another embodiment, the connector 26 is connected to the stimulation device via a chemical connection. For example, the stimulation device 20 could be adhered to the stimulation device 20 with a surgical adhesive. Examples of suitable surgical adhesives for bonding the stimulation device to the connector 26 include any of a variety of cyanoacrylates, derivatives of cyanoacrylates, or any other adhesive compound with acceptable toxicity to human gastrointestinal cells that provides the necessary adhesion properties required to secure the stimulation device 20 to the connector 26 for the desired amount of time.

The at least one connector 26 can be made of any biocompatible material that can be attached to the stimulation device 20 and can be secured in the vicinity of the target implant location by the attachment device 28 for the desired amount of time. The at least one connector 26 may take any of a variety of forms, including, but not limited to, a pin, a hook, a suture, a clip, or a loop. The connector 26 can be made of any of a variety of biocompatible materials including, but not limited to stainless steel, titanium, polyethylene, nylon, polytetrafluoroethylene (PTFE), and nitinol.

In an embodiment where the stimulation device 20 is configured to eventually self detach from the target location, the at least one connector 26 may be made of a degradable material that is degraded over a desired time. Examples of suitable degradable materials for fabrication of the fixation structure or structures include bioabsorbable or dissolvable materials such as polylactic acid (PLA) or copolymers of PLA and glycolic acid, or polymers of p-dioxanone and 1,4-dioxepan-2-one, as described in U.S. Pat. Nos. 6,285,897 and 6,698,056. A variety of absorbable polyesters of hydroxycarboxylic acids may be used, such as polylactide, polyglycolide, and copolymers of lactide and glycolide, as also described in U.S. Pat. Nos. 6,285,897, and 6,698,056. It may be desirable, in an embodiment where the stimulation device 20 is configured to eventually self detach from the target location, that the material of the connector 26 be the same as that of the fixation structure 31, thereby allowing for the release of all attachment mechanisms (the fixation structure(s) and the connector/attachment device) more or less simultaneously.

The connector 26 provides a mechanical connection for the stimulation device 20 to the attachment device 28. Generally, the attachment device 28 is secured in the vicinity of the target location and attached to the connector 26. The at least one attachment device 28 may take any of a variety of forms, including, but not limited to, a pin, a hook, a clip, or a loop. In one embodiment, the at least one attachment device 28 can be made of any of a variety of biocompatible materials, including, but not limited to stainless steel, titanium, polyethylene, nylon PTFE, or nitinol.

In an embodiment where the stimulation device 20 is configured to eventually self detach from the target location, the at least one attachment device 28 may be made of a degradable material that degrade over a desired time. Examples of suitable degradable materials for fabrication of the fixation structure or structures include bioabsorbable or dissolvable materials such as polylactic acid (PLA) or copolymers of PLA and glycolic acid, or polymers of p-dioxanone and 1,4-dioxepan-2-one, as described in U.S. Pat. Nos. 6,285,897 and 6,698,056. A variety of absorbable polyesters of hydroxycarboxylic acids may be used, such as polylactide, polyglycolide, and copolymers of lactide and glycolide, as also described in U.S. Pat. Nos. 6,285,897, and 6,698,056, the disclosure of which is incorporated herein by reference. It may be desirable, in an embodiment where the stimulation device 20 is configured to eventually self detach from the target location, that the material of the connector 26 be the same as that of the fixation structure 31, thereby allowing for the release of all attachment mechanisms (the fixation structure(s) and the connector/attachment device) more or less simultaneously.

In embodiments designed to self detach, either one or both of the connector 26 and the attachment device 28 can be made of degradable materials. In one embodiment, the connector 26 and the attachment device 28 are made of different materials, and in another embodiment, they are made of the same material. In another embodiment, the fixation device 31, the connector 26, and the attachment device 28 are all made of the same biodegradable material.

In one embodiment of the invention, the attachment device 28 is a commercially available endoscopic clip. Examples of endoscopic clips are available from a number of different manufacturers including, but not limited to Olympus America, Inc. (Melville, N.Y.), Wilson-Cook Medical (Winston-Salem, N.C.), and Boston Scientific (Natick, Mass.).

Exemplary endoscopic clips available from Olympus America, Inc. that could be utilized as attachment device 28 include, but are not limited to Clip Fixing Devices—Clip (catalog # HX-600-090, HX-600-090L, HX-600-0905, HX-600-134, and HX-600-135S); Clip Fixing Devices—QUICKCLIP™ (catalog # HX-200L-135.A, HX-200L-135.B, HX-200U-135.A, and HX-200U-135.B); and Quick-Clip2 (catalog # HX-201LR-135.A, HX-201LR-135.B, HX-201UR-135.B, and HX-201UR-135.B). Devices for deploying and attaching these exemplary commercially available attachment devices 28 from Olympus America, Inc. include, but are not limited to Clip Fixing Device—Rotatable Main Body (catalog # HX-5LR-1.A, HX-5LR-1.B, HX-5QR-1.A, HX-5QR-1.B, HX-6UR-1.A, and HX-6UR-1.B).

Exemplary endoscopic clips available from Wilson-Cook Medical that could be utilized as attachment device 28 include, but are not limited to the TriClip endoscopic clipping device. Exemplary endoscopic clips available from Boston Scientific that could be utilized as attachment device 28 include, but are not limited to the RESOLUTION™ Clip (order # M00522600, M00522601, M00522602, M00522610, M00522611, and M00522612).

In one embodiment of the invention, only one connector 26 and attachment device 28 are utilized for tethering the stimulation device 20 to the vicinity of the target location. In another embodiment, two connectors 26 and two attachment devices 28 are utilized. In yet another embodiment, more than two connectors 26 and more than two attachment devices 28 are utilized.

In one embodiment, only the at least one connector 26 is attached to the stimulation device 20 before the stimulation device 20 is implanted into the target location. In another embodiment, both the connector 26 and the attachment device 28 are connected to the stimulation device 20 before the stimulation device 20 is implanted into the target location. In yet another embodiment, neither the connector 26, nor the attachment device 28 are connected to the stimulation device 20 before the stimulation device 20 is implanted into the target location. In a further embodiment, the connector 26 is attached to the attachment device 28, but the connector 26 is not connected to the stimulation device 20.

As further shown in FIG. 1, in some embodiments, stimulation device 20 may communicate with an external controller 24 via wireless telemetry. Controller 24 may permit a user to activate stimulation device 20 and adjust stimulation parameters. For example, a patient 12 or other user may use controller 24 to start stimulation, stop stimulation, set stimulation duration, or adjust stimulation amplitude, frequency, pulse width and duty cycle. Wireless telemetry may be accomplished by radio frequency communication or proximal inductive interaction of controller 24 with stimulation device 20. External controller 24 may take the form of a portable, handheld device, like a pager or cell phone, that can be carried by patient 12.

Controller 24 may include an antenna that is attached to the body of patient 12 at a location proximate to the location of stimulation device 20 to improve wireless communication reliability. Also, in some embodiments, controller 24 may receive operational or status information from stimulation device 20, and may be configured to actively interrogate stimulation device to receive the information.

Examples of applications to which stimulation device 20 may be applied include trial screening of gastric electrical stimulation therapy for gastroparesis, or trial screening of gastric electrical stimulation for treatment of obesity, irritable bowel syndrome, functional dyspepsia, and gastroesophageal reflux disease. In these cases, stimulation device 20 may provide a convenient way to evaluate the potential efficacy of gastric electrical stimulation. In particular, with trial stimulation, a physician can determine whether long-term stimulation by surgical implantation of a stimulation device is appropriate for a particular patient. In addition, in some instances, stimulation device 20 may serve as a bridge between short-term relief of nausea and vomiting and the implantation of a long-term solution.

Other example applications include delivery of gastric electrical stimulation for treatment of nausea and/or vomiting resulting from chemotherapy, treatment of post-operative ileus, treatment of hyperemesis gravidarum, and temporary treatment of gastroparesis. Stimulation device 20 may be particularly useful for patients who have acute but severe symptoms but are refractory to drug therapy for such symptoms. Exemplary stimulation parameters for some of the above applications will be described in greater detail below.

Figure 3:
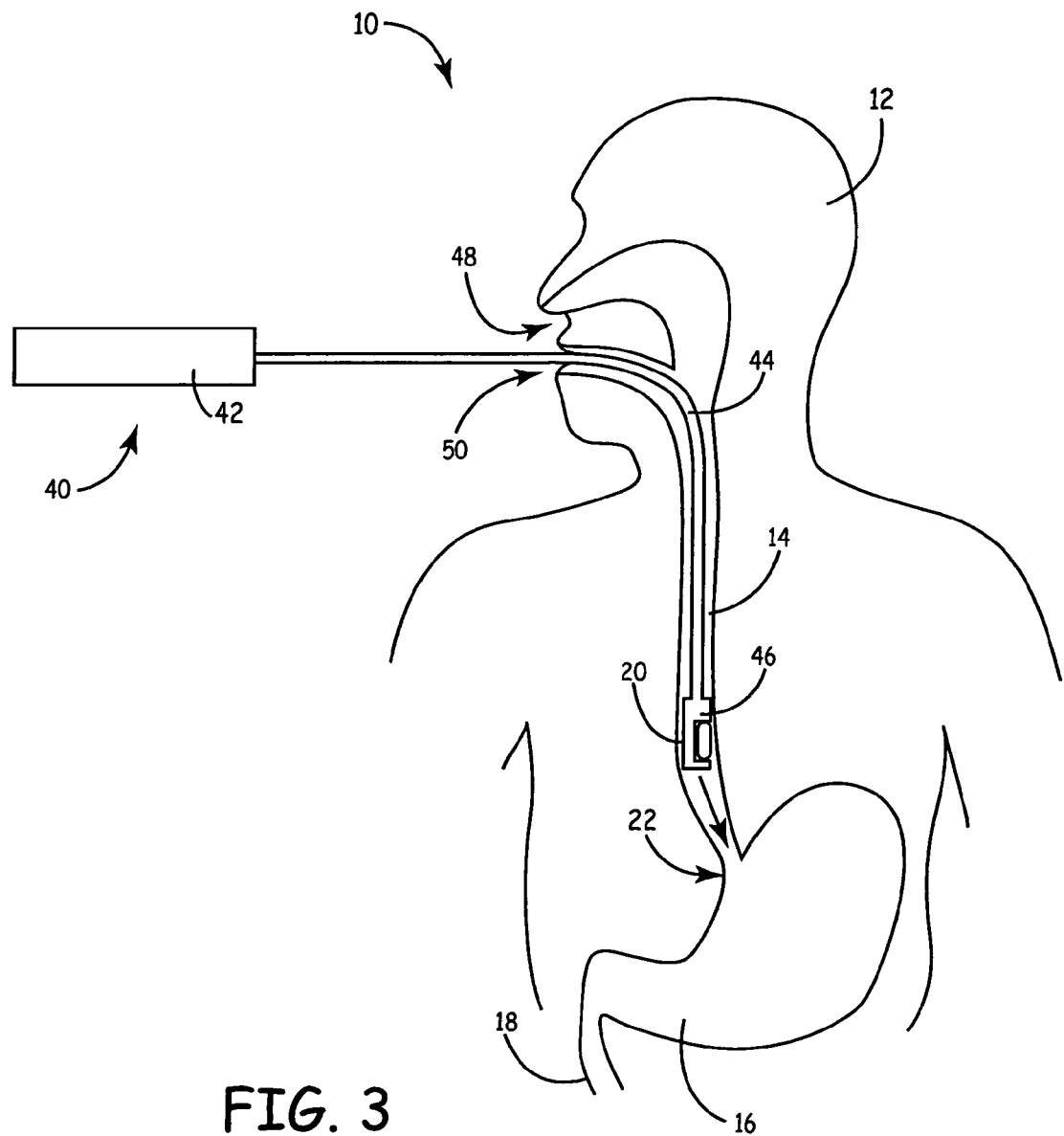
FIG. 3 is a schematic diagram illustrating deployment of the device of FIG. 2 within a patient's gastrointestinal tract.

FIG. 3 is a schematic diagram illustrating deployment and fixation of stimulation device 20 within the gastrointestinal tract of patient 12. As shown in FIG. 3, an endoscopic delivery device 40 serves to position and place stimulation device 20 within the gastrointestinal tract of patient 12. Delivery device 40 includes a proximal portion, referred to herein as a handle 42, and a flexible probe 44 that extends from handle 42 into the gastrointestinal tract of patient 12. Stimulation device 20 is coupled to a distal end 46 of delivery device 40 for delivery to a target location within the gastrointestinal tract. In the illustrated embodiment, stimulation device 20 is depicted as being in transit to a target location within stomach 16, which is accessed via esophagus 14 and LES 22. Distal end 46 of delivery device 40 enters esophagus 14, via either nasal cavity 48 or oral cavity 50, and extends through esophagus 14 to a desired placement location. Stimulation device 20 is attached to the mucosal lining at a target location within esophagus 14, stomach 16, or small intestine 18, as will be described in greater detail below, and the distal end 46 of delivery device 40 releases stimulation device 20.

Figure 4:
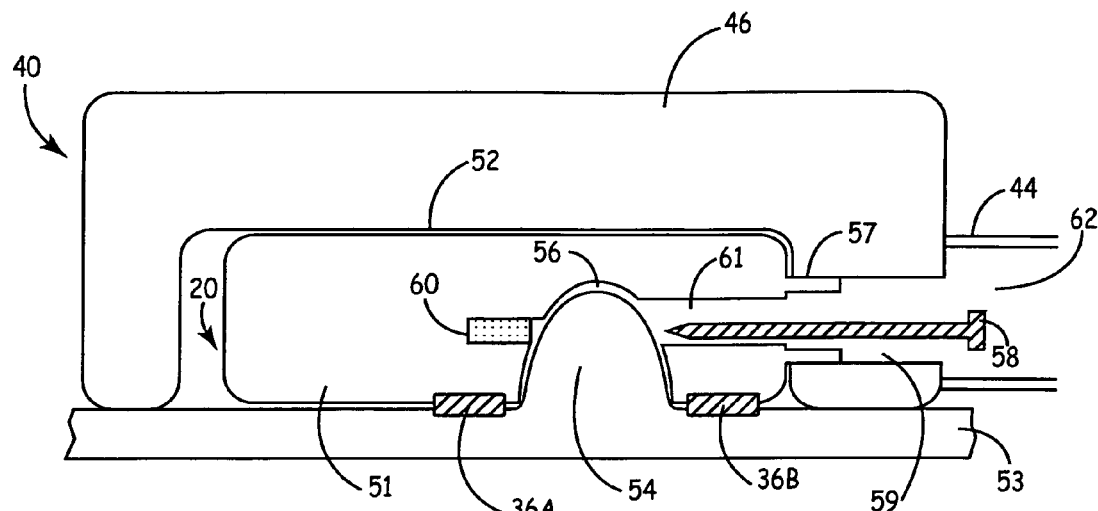
FIG. 4 is a cross-sectional side view illustrating positioning of a stimulation device within the gastrointestinal tract with a tissue fixation structure using a vacuum cavity and pin.

FIG. 4 is a cross-sectional side view illustrating positioning of a stimulation device 20 within the gastrointestinal tract with a fixation mechanism using a vacuum cavity and pin to secure tissue. During placement, stimulation device 20 is held within a placement bay 52 within distal end 46 of endoscopic delivery device 40. As shown in FIG. 4, stimulation device 20 has a capsule-like device housing 51, which may be substantially cylindrical in shape. Device housing 51 may be formed from a variety of biocompatible materials such as stainless steel or titanium. A coupling collar 57 serves to secure a proximal end of device housing 51 within a channel 59 defined by distal end 46 of delivery device 40.

Device housing 51 includes a pulse generator (not shown in FIG. 4), electrodes 36A, 36B, and a fixation structure. Electrodes 36A, 36B are coupled to the pulse generator to deliver stimulation energy to tissue at the target site. A physician guides endoscopic delivery device 40 to place electrodes 36A, 36B in contact with a mucosal lining 53 at the target location of the gastrointestinal tract. Delivery device 40 may include viewing optics to permit the physician to visualize the target location and observe implantation of stimulation device 20. Alternatively, an independent viewing endoscope may be inserted with delivery device 40, or external viewing techniques such as radiography or fluoroscopy may be used.

In the example of FIG. 4, the fixation structure includes a vacuum cavity 56 defined by device housing 51 and a tissue securing pin 58. Upon engagement of stimulation device 20 with mucosal lining 53, the physician activates a vacuum source (not shown) to apply negative pressure to vacuum cavity 56 via a vacuum port 61. The vacuum source is coupled to an internal lumen 62 within flexible probe 44, and is in fluid communication with vacuum port 61. The negative vacuum pressure serves to draw a portion 54 of mucosal lining 53 into vacuum cavity 56. Tissue securing pin 58 can then be advanced through the tissue 54 held in vacuum cavity 56 to thereby penetrate the tissue 54 and attach device housing 51 to the mucosal lining 53.

The volume of tissue 54 drawn into vacuum cavity 56 and the depth of penetration of pin 58 may be selected to avoid penetration through the wall of the gastrointestinal tract, e.g., the esophageal wall or stomach wall. As an example, it may be desirable to limit the depth of penetration to a range of approximately 1 mm to 15 mm when the site comprises the antrum of the stomach or in the range of approximately 1 mm to 10 mm when the site comprises corpus or fundus to ensure that the fixation structure does not extend substantially through the wall of the gastrointestinal lumen.

Figure 5:
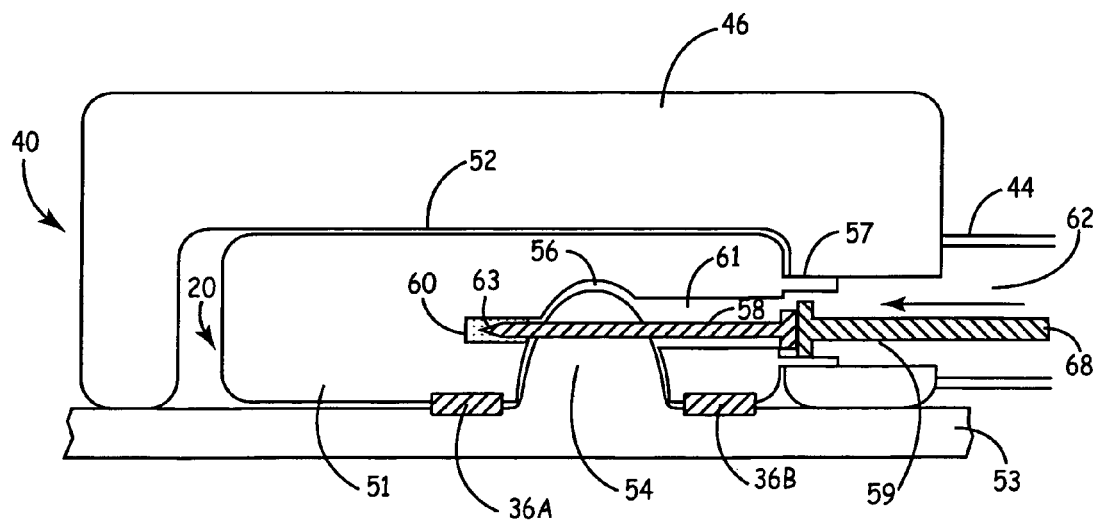
FIG. 5 is a cross-sectional side view of the device of FIG. 4 with the tissue securing pin advanced through tissue within the vacuum cavity.

FIG. 5 is a cross-sectional side view of the stimulation device 20 of FIG. 4 with the tissue securing pin 58 advanced through tissue within the vacuum cavity 56. As shown in FIG. 5, the physician advances a rod-like member 68 within internal lumen 62 of flexible probe 44 to drive pin 58 into the tissue 54 held in vacuum cavity 56. A distal tip 63 of pin 58 may be received in a bushing 60. Once pin 58 has secured tissue 54, the physician turns off the vacuum source, and releases device housing 51 from placement bay 52 of distal end 46 of delivery device 40. Additional details concerning a similar fixation structure for stimulation devices can be found in U.S. Pat. Nos. 6,285,897, and 6,698,056.

Figure 6:
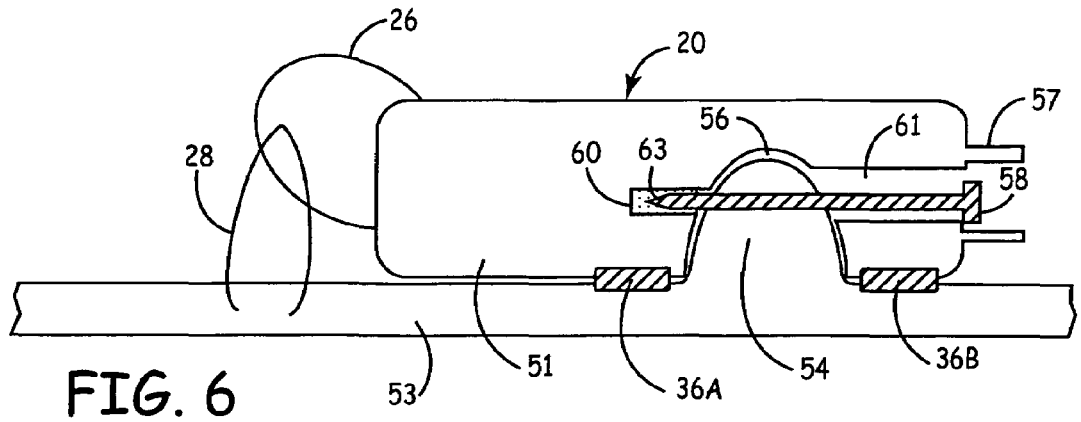
FIG. 6 is a cross-sectional side view of the device of FIG. 5 following removal of an endoscopic delivery device.

FIG. 6 is a cross-sectional side view of stimulation device 20 of FIG. 5 implantation and before tethering. As shown in FIG. 6, pin 58 holds device 20 securely in place relative to mucosal lining 53. At the same time, electrodes 36A, 36B are placed in contact with mucosal lining 53 to thereby deliver the electrical stimulation waveform to the target location. Electrodes 36A, 36B may operate as anode and cathode, respectively, for delivery of electrical stimulation. Electrodes 36A, 36B may be mounted to device housing 51 so that the electrodes are exposed to body tissue. For example, electrodes 36A, 36B may be in the form of conductive pads on one or both sides of vacuum cavity 56, or bands or rings that encircle the device housing on one or both sides of the vacuum cavity.

The stimulation device shown in FIG. 6 depicts an at least one connector 26, in contact with an attachment device 28, which is functioning to tether the stimulation device 20 to the vicinity of the target location. Once the stimulation device 20 has been deployed and attached via the fixation structure, the stimulation device 20 can then be tethered to the vicinity of the target location. In one embodiment, the connector 26 can be attached to the device housing 51, if necessary. In embodiments where the connector 26 is attached to the device housing 51 before implantation, this step is not necessary. The attachment device 28 is then secured to the mucosal lining 53. The details of the attachment of the attachment device 28 to the mucosal lining 53 will depend on the particular type of attachment device 28 that is being utilized, and will be well within the level of ordinary skill in the art. The attachment device 28 is then connected to the connector 26. Again, the details regarding the attachment of the connector 26 to the attachment device 28 will depend on the particular types being used and will be within the level of ordinary skill in the art. It should also be understood that there is no particular order in which the connector 26 is attached to the device housing 51 of the stimulation devices 20, the connector 26 is attached to the attachment device 28, and the attachment device 28 is attached to the mucosal lining 53. The order in which these are done can depend at least in part on the particular types of connectors and attachment devices used, the attachment of the connector to the stimulation device, the way in which the stimulation device is delivered to the target location, and the particular preferences of the surgeon. It should also be understood that some, all, or more of these connections can be made before the stimulation device 20 is deployed into the patient.

In one embodiment, tissue securing pin 58 may itself form an electrode, e.g., the cathode. In this case, one or more electrodes 36A, 36B may serve to create a common anode with tissue securing pin 58 forming the cathode. Bushing 60 may be electrically conductive and form part of an electrical conduction path between tissue securing pin 58 and the pulse generator housed within device housing 51. As tissue 54 captured within vacuum cavity 56 deteriorates, however, electrical conductivity between pin 58 and mucosal lining 53 may decrease. Therefore, it may be desirable to use electrodes 36A, 36B as anode and cathode in some applications for longer term delivery of electrical stimulation.

If a fixation structure that penetrates mucosal lining 53, such as pin 58, also serves as an electrode, it may be desirable to coat the surface of the fixation structure. For example, the fixation structure can be coated with a porous platinized structure to reduce polarization and/or an anti-inflammatory agent that inhibits inflammation that can negatively affect the ability to efficiently deliver electrical stimulation. The anti-inflammatory agents can be embedded into a monolithic controlled release device (MCRD) carried by the fixation structure. Such anti-inflammatory agents include steroids, anti-bacterial agents, baclofen, dexamethasone sodium phosphate and beclomethasone phosphate.

Figure 7:
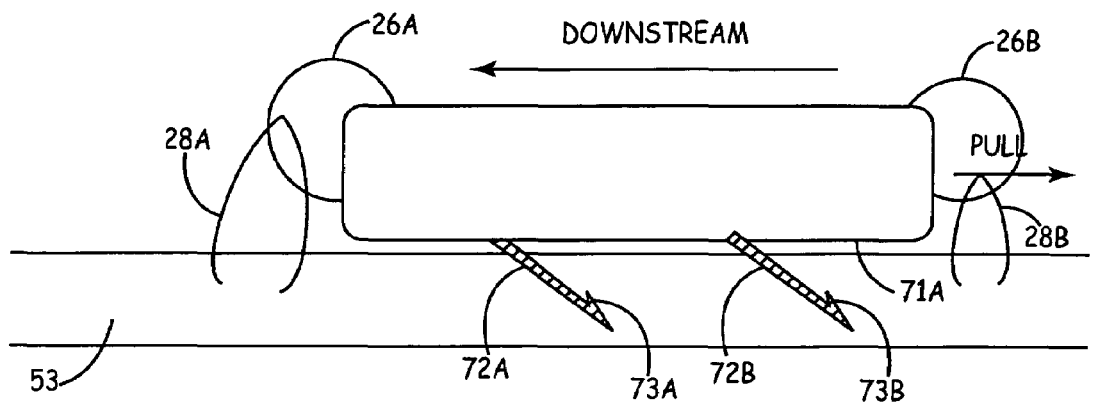
FIG. 7 is a side view of a stimulation device within the gastrointestinal tract with a tissue fixation structure using a pair of barbed hooks.

FIG. 7 is a side view of another stimulation device 70A within the gastrointestinal tract with a fixation structure using a pair of barbed hooks 72A, 72B to penetrate tissue within mucosal lining 53. Hooks 72A, 72B may be sized to limit the depth of penetration as described above, yet securely attach stimulation device 70A to the mucosal lining 53. Stimulation device 70A may have a capsule-like device housing 71A, and may generally conform to stimulation device 20 of FIGS. 4-6. In the embodiment of FIG. 7, however, barbed hooks 72A, 72B function as the fixation structure and also form an anode and cathode for delivery of stimulation energy. A physician may deliver stimulation device 70 using an endoscopic device similar to delivery device 40 of FIGS. 3-6.

As an example, hooks 72A, 72B and associated barbs 73A, 73B may be angled upstream within the esophagus, as shown in FIG. 7, so that device housing 71A can be maneuvered downstream without snagging the mucosal lining 53. Upon reaching the target location, e.g., within esophagus 14 or stomach 16, the physician may pull back on delivery device 20 to maneuver device housing 70A upstream and thereby snag and penetrate the mucosal lining 53 with hooks 72A, 72B.

Upon penetration of mucosal lining 53, hooks 72A, 72B secure stimulation device 70A in place at the target location, and the physician withdraws endoscopic delivery device 40. Stimulation device 70 then delivers electrical stimulation via hooks 72A, 72B, which are formed from electrical conductive material and form an anode and cathode, respectively. Although hooks 72A, 72B are described as serving as both the fixation structure and electrodes, in some embodiments, dedicated electrodes may be provided in addition to hooks 72A, 72B. In this case, hooks 72A, 72B may serve only for attachment, while electrodes are mounted to device housing 71A for contact with mucosal lining 53. Once this embodiment of the stimulation device 71A is fixed to the mucosal lining 53 the connectors 26A and 26B, and attachment devices 28A and 28B can be put in place in order to tether the stimulation device 71A to the mucosal lining. The attachment of the stimulation device 71A to the mucosal lining 53 via the connectors 26A and 26B and the attachment devices 28A and 28B can be accomplished as explained above.

Figure 8:
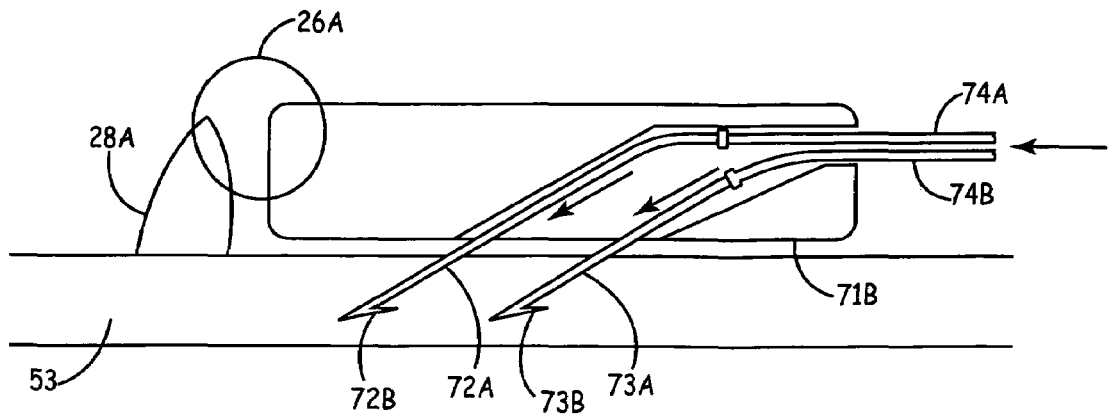
FIG. 8 is a side view of a stimulation device within the gastrointestinal tract with an alternative tissue fixation structure using a pair of barbed hooks.

FIG. 8 is a side view of a stimulation device 70B within the gastrointestinal tract with an alternative fixation structure using a pair of barbed hooks 72A, 72B. In the example of FIG. 8, a physician actuates elongated translation members 74A, 74B via endoscopic delivery device 40 to push hooks 72A, 72B and extend them outward from device housing 71B to penetrate tissue within mucosal lining 53. During delivery to a target location, hooks 72A, 72B are withdrawn within device housing 71B. When device 70B arrives at the target location, however, the physician moves translation members 74A, 74B forward to extend hooks 72A, 72B. Translation members 74A, 74B may take the form of flexible push rods that force hooks 72A, 72B outward, but are then withdrawn from device housing 71B and removed from the body of patient 12 via delivery device 40. After deployment and fixation, the stimulation device 70B can then be tethered via connector 26 and attachment device 28 as discussed above.

Figure 9:
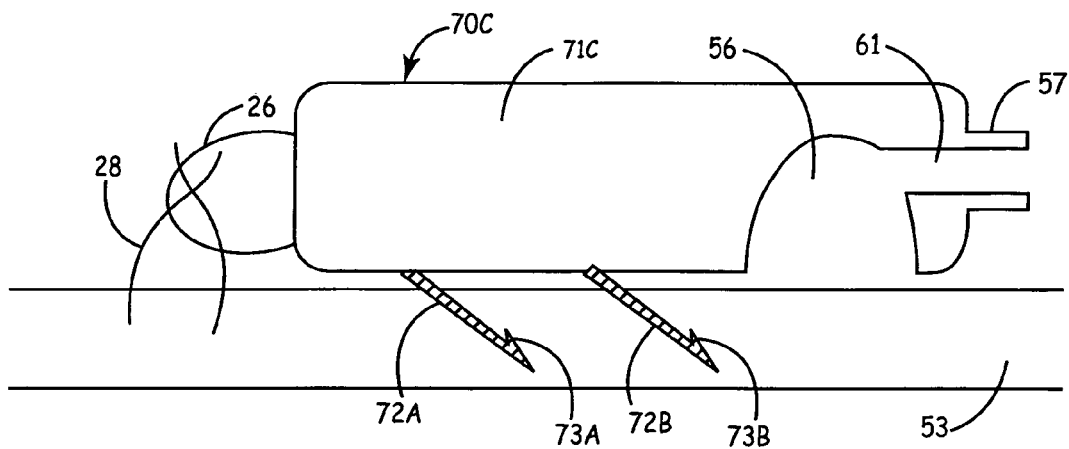
FIG. 9 is a bottom plan view of an alternative stimulation device with a vacuum cavity and a pair of tissue securing pins.

FIG. 9 is a cross-sectional side view of a stimulation device 70C with a fixation structure that combines barbed hooks 72A, 72B with a vacuum cavity 56 and vacuum port 61 and connector 26 and attachment device 28. Stimulation device 70C generally conforms to device 70A of FIG. 7, but further includes vacuum cavity 56 to draw mucosal lining 53 toward device 70A and thereby stabilize device housing 71C against the mucosal lining during attachment of hooks 72A, 72B. In some embodiments, vacuum pressure may aid in driving hooks 72A, 72B into mucosal lining 53. Upon release of vacuum pressure, hooks 72A, 72B serve to secure stimulation device 70C to mucosal lining 53. Hooks 72A, 72B may be formed of conductive material to serve as electrodes, or separate electrodes may be mounted to device housing 71C. After deployment and fixation, the stimulation device 70C can then be tethered via connector 26 and attachment device 28 as discussed above.

Figure 10:
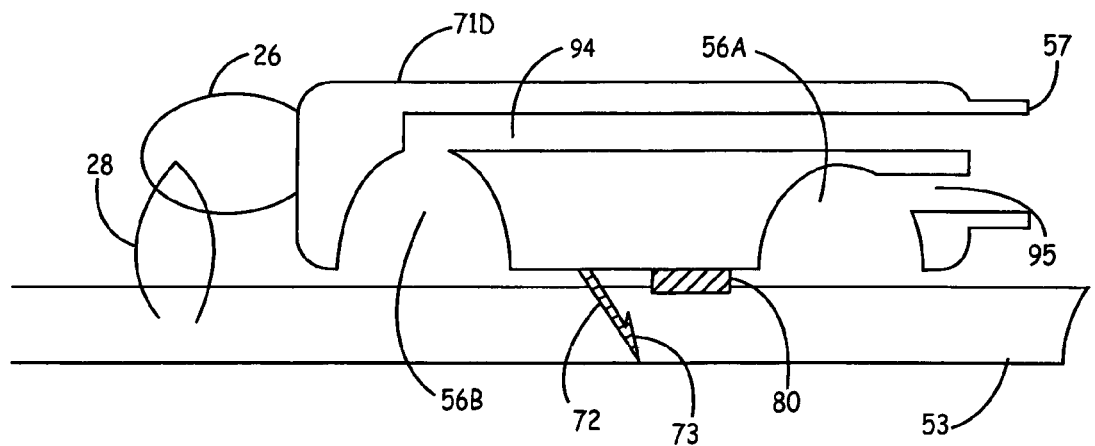
FIG. 10 is a cross-sectional side view of a stimulation device with a fixation structure that combines barbed hooks with a vacuum cavity.

FIG. 10 is a cross-sectional side view of a stimulation device 70D with a fixation structure that combines barbed hook 72 with a pair of vacuum cavities 56A, 56B, and connector 26 and attachment device 28. Vacuum pressure applied to vacuum cavities 56A, 56B via vacuum ports 94, 95, respectively, draws mucosal lining 53 toward device 76C to thereby stabilize device body 71D against the mucosal lining, or aid in driving hook 72 into the mucosal lining. Upon release of vacuum pressure, hook 72 serves to secure stimulation device 70D to mucosal lining 53. Hook 72 may be formed of conductive material to serve as an electrode, e.g., in combination with electrode 80 mounted to device housing 71D. Alternatively, separate electrodes may be mounted to device housing 71D. In some embodiments, hook 72 may be extended from device housing 71D by actuating a translating member. After deployment and fixation, the stimulation device 70D can then be tethered via connector 26 and attachment device 28 as discussed above.

FIG. 11 is cross-sectional side view of another stimulation device 105 with a capsule-like device housing 106. FIG. 12 is a top view of stimulation device 105 of FIG. 11. As shown in FIGS. 11 and 12, stimulation device housing 106 includes a raised feature 108, an internal circuit board 110 carrying components 114, 116 and coupled to a battery 112, a ring-like electrode 115, and a screw-like extension 118 extending from an end of the housing opposite the raised feature. Although not shown in FIG. 11, 12, or 13, the stimulation device 105 may be pre-attached to the connector 26, or the connector 26 and the attachment device 28.

Ring-like electrode 115 may extend about the entire periphery or a portion of the periphery of stimulation device housing 106. In the illustrated embodiment, screw-like extension may be formed from an electrically conductive material, in which case ring-like electrode 115 and screw-like extension 118 may serve as an anode and cathode, respectively, for stimulation device 105. In other embodiments, two or more ring-like electrodes, similar to electrode 115, may be provided to serve as cathode and anode for delivery of stimulation energy.

Stimulation device 105 is capable of delivery via an endoscopic delivery device, but includes an axial fixation structure rather than a lateral fixation structure. In particular, screw-like extension 118 extends coaxially with the longitudinal axis of stimulation device 105. During placement of stimulation device 105, screw-like extension 118 extends distally from the delivery device. Helical screw-like extension 118 may include one or more helical coil turns terminating in sharpened tip 119.

FIG. 13 is a cross-sectional side view of stimulation device 105 of FIG. 11, illustrating delivery via an endoscopic delivery device 120. As shown in FIG. 13, device housing 106 is disposed at a distal end 121 of delivery device 120. Raised feature 108 engages a recess 123 within a working member 125 of delivery device 120. Recess 123 is coupled to a vacuum port 122. A physician applies vacuum pressure to raised feature 108 via recess 123 and vacuum line 122 to hold device housing 106 in place during delivery to the target location within the gastrointestinal tract.

When distal end 121 of delivery device 120 reaches a target location, the physician rotates working member 125 to rotate stimulation device 105 and thereby screw extension 118 into the target site. The physician then deactivates the vacuum pressure, and advances a translation member 124 to push stimulation device 105 out of delivery device 120 to ensure separation, and withdraws delivery device 120. Device housing 106 may include one of more longitudinal markings 127 to permit a physician to see, with endoscopic visualization, to what extent stimulation device 105 has been rotated during screw-in insertion into tissue. Alternatively, the markings 127 may be radio-opaque to permit external visualization using radiography or fluoroscopy.

Figure 14:
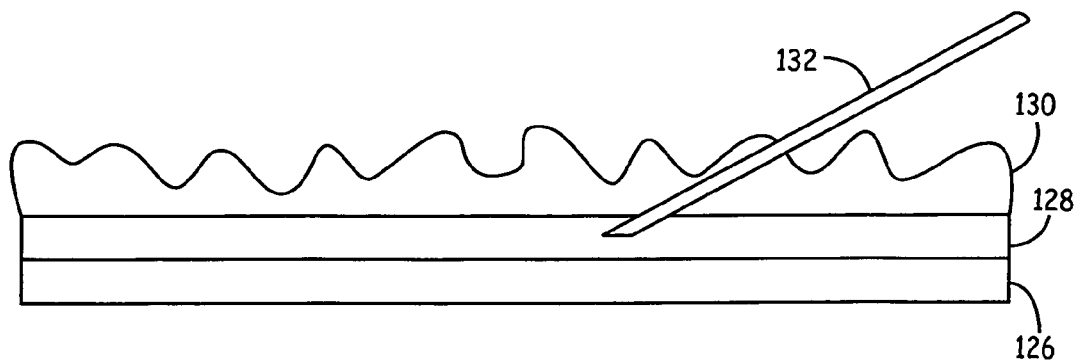
FIG. 14 is a schematic diagram illustrating insertion of a stylet into the mucosal lining of the stomach.

FIG. 14 is a schematic diagram illustrating insertion of a stylet 132 into the mucosal lining of the stomach as part of an exemplary procedure for implantation of stimulation device 105 of FIGS. 11-12. As shown in FIG. 3, stylet 132 is endoscopically guided to a target location within the lumen of the stomach. At the target location, the stomach lining includes muscle layer 126, submucosal layer 128 and mucosal layer 130. Stylet 132 penetrates submucosal layer 128.

Figure 15:
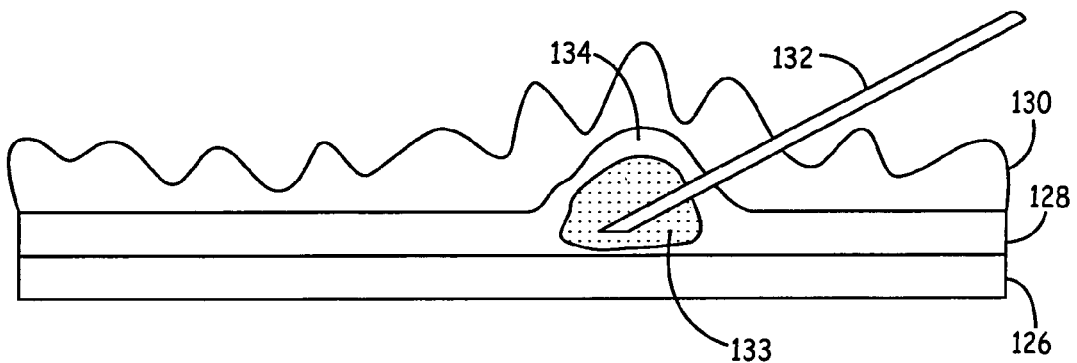
FIG. 15 is a schematic diagram illustrating introduction of fluid through the stylet of FIG. 14 into the implant pocket shown in FIG. 14.

FIG. 15 is a schematic diagram illustrating introduction of fluid 133, such as saline, through stylet 132 to create an expanded implant pocket 134. To insert stimulation device 105 into sub-mucosal layer 128 so that the screw-like extension 118 makes electrical contact with muscle tissue and associated sub-mucosal plexus or myenteric plexus, it is necessary to first create pocket 134 in the sub-mucosal layer. The volume of fluid 133 introduced by stylet 132 expands submucosal layer 128 to create a pocket-like protrusion. The introduction of saline into sub-mucosal layer 128 results in a sort of a saline "blister."

Figure 16:
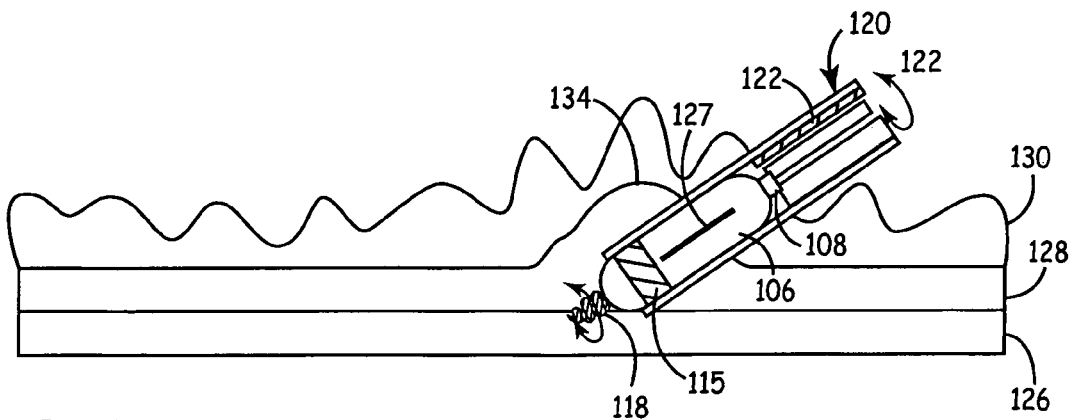
FIG. 16 is a schematic diagram illustrating implantation of the device of FIG. 1 into the implant pocket shown in FIG. 15.

Upon creation of the implant pocket 134, the physician withdraws stylet 132 and makes a small incision in the blister with a small endoscopic cutting instrument. The physician then introduces endoscopic delivery device 120 through the incision opening in the blister to deliver stimulation device 105, as shown in FIG. 16. When the screw-like extension makes contact with muscle layer 126 of the stomach, the physician screws the capsule-like stimulation device 105 into the muscle layer, e.g., with one turn of the device.

Figure 17:
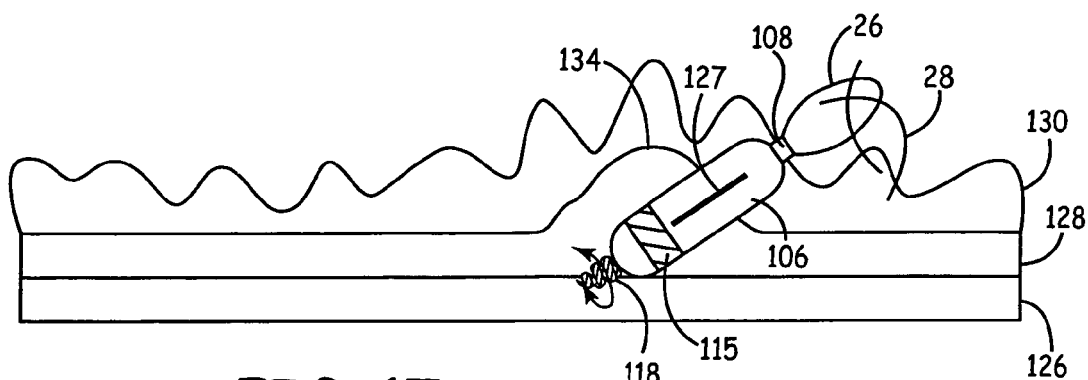
FIG. 17 is a schematic diagram illustrating the device of FIG. 1 implanted in the mucosal lining of the stomach.

When translation member 124 is advanced to force stimulation device housing 106 out of delivery device 120, screw-like extension 118 is lodged in the muscle layer tissue. Then, the physician deactivates vacuum pressure, and withdraws endoscopic delivery device 120 slightly so that the proximal end of the stimulation device 105 is fully visible. The physician then places the capsule-like housing 106 placed fully within pocket 134, and closes the pocket, e.g., with sutures or clips applied endoscopically. Then, the physician withdraws delivery device 120 from patient 12, leaving stimulation device 105 in place within the stomach lining. After the stimulation device 105 is in place within the stomach lining, the connector 26 and the attachment device 28 can be put in place to tether the stimulation device 105 to the stomach lining. In the example that is depicted in FIG. 17, the connector 26 is attached in the vicinity of the raised feature 108. The attachment device 28 is then coupled to the connector 26 to tether the stimulation device 105 to the stomach lining. The details regarding the attachment of the connector 26 to the stimulation device 105, coupling the attachment device 20 to the connector 26, and fixing the attachment device 28 to the stomach lining were discussed above, and will not be repeated here. In this manner, a self-contained, capsule-like stimulation device 105 is securely implanted and tethered within the patient, and operates without the need for trans-nasal or trans-oral leads that could otherwise cause discomfort for the patient or result in dislodgement of electrodes.

Figure 18:
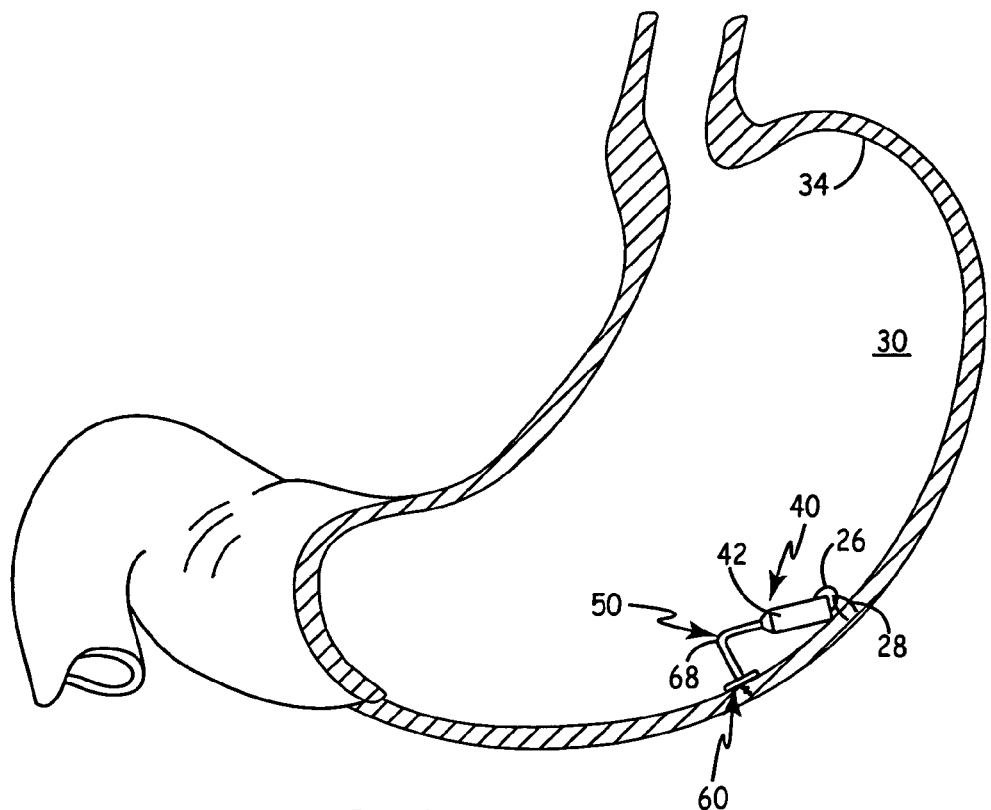
FIG. 18 is a diagram of a device of the invention implanted in the stomach.

FIG. 18 depicts another exemplary embodiment of a stimulation device 40 that is fixed and tethered to, in this example, the stomach 30. One embodiment of the invention that may be similar to this embodiment can be found in U.S. Pat. No. 6,754,536, the disclosure of which is incorporated by reference herein. The stimulation device 40 includes at least one electrode 60, which in this example also functions as the fixation structure. The stimulation device 40 also includes an elongated flexible member 50 that extends away from the housing 42. The elongated flexible member 50 extends away from the housing 42 to the end of the stimulation device 40 with the electrode and fixation mechanism s60. The electrode and fixation mechanism 60 is configured to penetrate the mucosa of the stomach wall 34, or the mucosa of some other portion of the gastrointestinal tract. The stimulation device 40 also includes, either before it is implanted, or after, a connector 26. The connector 26 is attached to the housing 42 of the stimulation device. The attachment device 28 can then be coupled to the connector 26 and fixed to the stomach wall 34. In one embodiment, the connector 26 is attached on the housing 42 at a location that is somewhat removed from the elongated flexible member 50. In yet another embodiment, the connector 26 is attached at the opposite end of the housing 42 as the elongated flexible member 50.

In one embodiment, tethering the connector 26 via the attachment device 28 to the stomach causes the elongated flexible member 50 to bend 68. In another embodiment, the stimulation device 40 is configured with bend 68 preformed or formed upon release from the delivery device, and tethering it via connector 26 and attachment device 28 merely works in concert with the bend 68 in the stimulation device 40.

Figure 19:
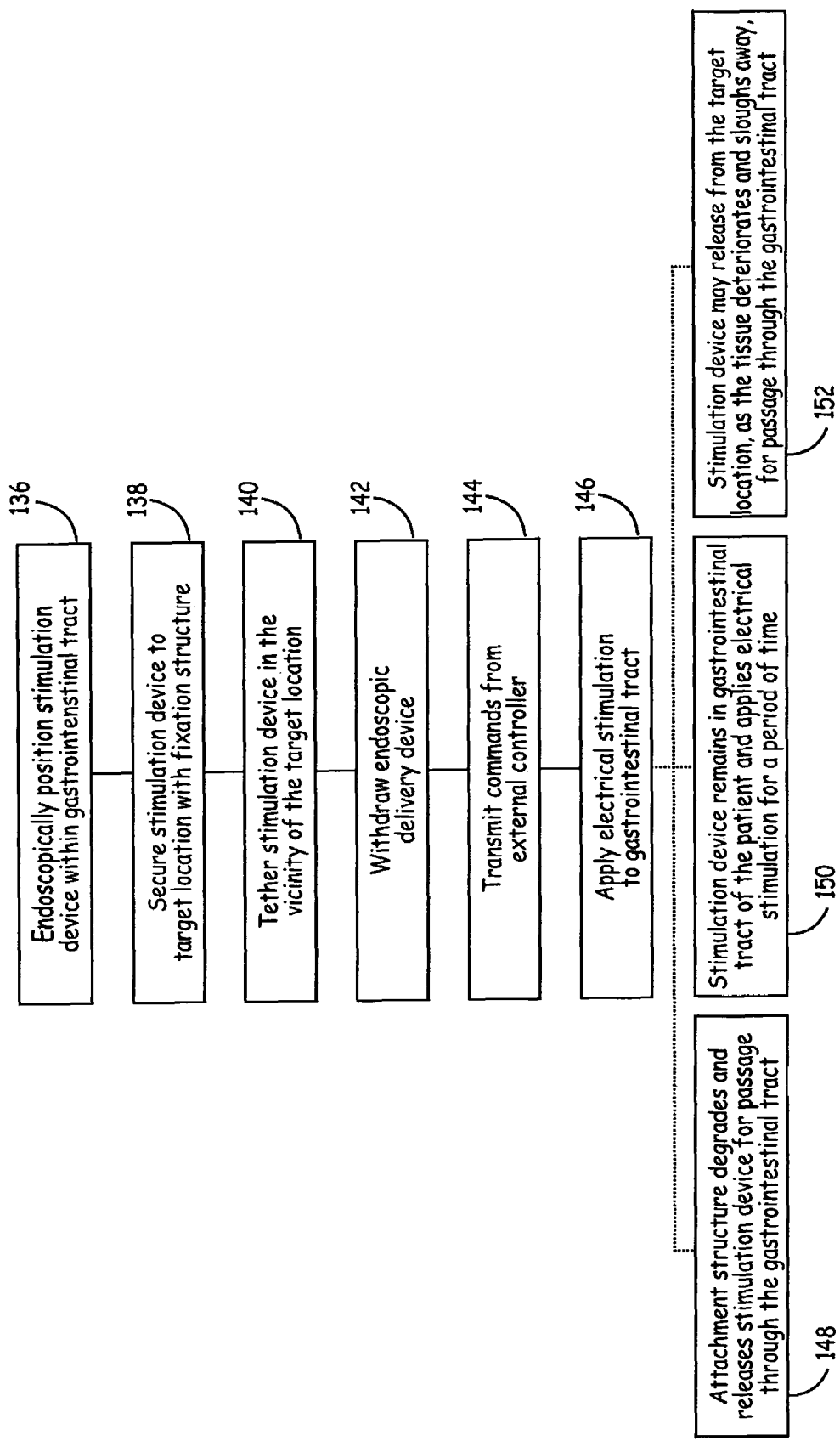
FIG. 19 is a flow diagram illustrating implantation and operation of a gastrointestinal electrical stimulator.

FIG. 19 is a flow diagram illustrating implantation and operation of a gastrointestinal electrical stimulator. As shown in FIG. 19, the physician positions the capsule-like stimulator at a target location within the gastrointestinal tract with an endoscopic delivery device (136) and then secures the stimulator to tissue at the target location using a fixation structure carried by the stimulator (138). Then the stimulation device is tethered to the vicinity of the target location using at least one connector and attachment device (140). Upon withdrawing the endoscopic delivery device from the patient (142), the physician may transmit one or more commands to the implanted stimulation device using an external controller to activate the stimulation device (144). Alternatively, the stimulation device may be self-activating upon deployment from the endoscopic delivery device. If an external controller is provided, in some embodiments, it also may be used to adjust stimulation parameter settings.

Upon activation, the capsule-like stimulation device applies electrical stimulation waveform to the target location within the gastrointestinal tract (146). The stimulation device continues to operate until battery resources are exhausted, the device is removed, or turned off (150), or in some embodiments in which the fixation structure is made from a degradable material, the fixation structure degrades and releases the stimulation device from the target location to permit the stimulator to pass through the gastrointestinal tract (150). As a further alternative, the stimulator may release from the tissue as the tissue deteriorates and sloughs away, permitting the stimulation device to pass through the gastrointestinal tract (152).

The preceding specific embodiments are illustrative of the practice of the invention. It is to be understood, therefore, that other expedients known to those skilled in the art or disclosed herein may be employed without departing from the invention or the scope of the claims. For example, the invention is not limited to deployment of a stimulation device at a particular location within the gastrointestinal tract. In various embodiments, a stimulation device may be located anywhere within the gastrointestinal tract. For example, the stimulation device may be affixed along or to any of the other structures and organ walls along the gastrointestinal tract, including the colon, small intestine, stomach, or the esophagus.

In addition, the invention is not limited to application for any particular disorder, condition or affliction. As examples, the invention may be applicable to treatment of symptoms secondary to a variety of conditions, such as nausea or vomiting secondary to gastroparesis, functional dyspepsia, chemotherapy, post-operative ileus, or even pregnancy. Also, the invention may be applicable not only to treat particular short-term or mid-term symptoms, but also for trial stimulation to evaluate the efficacy of stimulation for a variety of treatments such as more long-term treatment of gastroparesis, obesity, irritable bowel syndrome, functional dyspepsia, and gastroesophageal reflux disease, to name a few.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A stimulation device for electrical stimulation of a target location of a gastrointestinal tract of a patient, the device comprising:
   a device housing sized for introduction into a gastrointestinal tract;
   an electrical pulse generator, mounted within the device housing, to generate an electrical stimulation waveform;
   one or more electrodes electrically coupled to the electrical pulse generator and mounted to the device housing to deliver the electrical stimulation waveform to the gastrointestinal tract;
   a fixation structure which attaches the stimulation device to the target location of the gastrointestinal tract;
   a biodegradable connector, wherein the device housing is attached to the connector via a chemical connection; and
   an attachment device, different from the fixation structure, coupled to the biodegradable connector, wherein the stimulation device is configured to be tethered to an area around the target location using the attachment device.

2. The stimulation device of claim 1, wherein the fixation structure is one or more pins, hooks, barbs, screws, sutures, clips, pincers, staples, or tacks.

3. The stimulation device of claim 1, wherein the attachment device is one or more pins, hooks, clips, or loops.

4. The stimulation device of claim 3, wherein the attachment device is a surgical clip.

5. The stimulation device of claim 1, wherein the attachment device is biodegradable.

6. The stimulation device of claim 5, wherein the attachment device is polylactic acid (PLA), a copolymer of PLA and glycolic acid, a polymer of p-dioxanone, a polymer of 1,4-dioxepan-2-one, or an absorbable polyester of hydroxycarboxylic acid.

7. A stimulation system for electrical stimulation of a target location of a gastrointestinal tract of a patient, said system comprising:
   a stimulation device comprising:
      a device housing;
      an electrical pulse generator, mounted within the device housing, to generate an electrical stimulation waveform;
      one or more electrodes electrically coupled to the electrical pulse generator and mounted to the device housing to deliver the electrical stimulation waveform to the gastrointestinal tract; and
      a fixation structure to attach the device housing to a target location within the gastrointestinal tract of the patient;
   a biodegradable connector, wherein the device housing is attached to the connector via a chemical connection; and
   an attachment device, different from the fixation structure, coupled to the biodegradable connector, wherein the connector and the attachment device tethers the stimulation device to an area near the target location.

8. The stimulation system of claim 7, wherein the fixation structure is one or more pins, hooks, barbs, screws, sutures, clips, pincers, staples, or tacks.

9. The stimulation system of claim 7, wherein the attachment device is one or more pins, hooks, clips, or loops.

10. The stimulation system of claim 9, wherein the attachment device is a surgical clip.

11. The stimulation system of claim 7, wherein the attachment device is biodegradable.

12. The stimulation system of claim 11, wherein the attachment device is polylactic acid (PLA), a copolymer of PLA and glycolic acid, a polymer of p-dioxanone, a polymer of 1,4-dioxepan-2-one, or an absorbable polyester of hydroxycarboxylic acid.

* * * * *